(12) United States Patent
Baerlecken et al.

(10) Patent No.: US 11,199,549 B2
(45) Date of Patent: *Dec. 14, 2021

(54) METHODS AND MEANS FOR DIAGNOSING SPONDYLARTHRITIS USING AUTOANTIBODY MARKERS

(71) Applicants: Niklas Thomas Baerlecken, Hannover (DE); Torsten Witte, Hannover (DE)

(72) Inventors: Niklas Thomas Baerlecken, Hannover (DE); Torsten Witte, Hannover (DE)

(73) Assignee: MEDIZINISCHE HOCHSCHULE HANNOVER, Hannover (DE)

( * ) Notice: Subject to any disclaimer, the term of this patent is extended or adjusted under 35 U.S.C. 154(b) by 562 days.

This patent is subject to a terminal disclaimer.

(21) Appl. No.: 15/883,126

(22) Filed: Jan. 30, 2018

(65) Prior Publication Data
US 2018/0224463 A1    Aug. 9, 2018

Related U.S. Application Data

(62) Division of application No. 13/816,962, filed as application No. PCT/EP2011/004098 on Aug. 16, 2011, now Pat. No. 9,915,664.

(30) Foreign Application Priority Data

Aug. 16, 2010 (EP) .................................. 10172861

(51) Int. Cl.
G01N 33/564 (2006.01)
G01N 33/68 (2006.01)
C12Q 1/48 (2006.01)
A61K 38/45 (2006.01)

(52) U.S. Cl.
CPC ......... *G01N 33/6854* (2013.01); *A61K 38/45* (2013.01); *C12Q 1/485* (2013.01); *C12Y 207/1101* (2013.01); *G01N 33/564* (2013.01); *G01N 2333/70596* (2013.01); *G01N 2800/102* (2013.01); *G01N 2800/105* (2013.01); *G01N 2800/50* (2013.01)

(58) Field of Classification Search
None
See application file for complete search history.

(56) References Cited

U.S. PATENT DOCUMENTS

2004/0098756 A1 * 5/2004 Singh .................. C12N 9/1247
800/14

OTHER PUBLICATIONS

Yang et al., Identification and characterization of IgA antibodies against β2-glycoprotein I in childhood Henoch-Schölein purpura, Br. J. Dermatol., (2012), 167(4), p. 874-881 (Year: 2012).*
Stein et al., CD74: A New Candidate Target for the Immunotherapy of B-cell Neoplasms, Clin. Cancer Res, 13(18 Suppl), (2007), (9 pages) (Year: 2007).*
Nagasubramanian et al., Immunological Investigations in Chronic Simple Glaucoma, Trans. Ophthalmol Soc. U K., 98(1), (1978), (abstract) (Year: 1978).*

* cited by examiner

*Primary Examiner* — Ellen J Marcsisin
(74) *Attorney, Agent, or Firm* — W&C IP (57) ABSTRACT

The present invention relates generally to methods for diagnosing the presence or the risk of development or the therapy control of spondyloarthritis (Spa), in particular, of ankylosing spondylitis (AS) and undifferentiated spondyloarthritis in a subject, in particular in mammals. In addition, the present invention relates to test kits for use in the diaposis of the presence or the risk of development, or for the therapy control of Spa, like AS and undifferentiated spondyloarthritis, in a subject. In particular, the present invention relates to a method for diagnosing the presence or the risk of development, or for the therapy control of Spa, like AS and undifferentiated spondyloarthritis, it a subject analysing for the presence of autoantibodies against CD74 and/or IKBKB in a subject. The presence of autoantibodies against CD74 and/or IKBKB is indicative for the presence or the risk of development, or for the therapy control of Spa, like AS and undifferentiated spondyloarthritis. In particular, detection of the presence of autoantibodies against CD74 and/or IKBKB allows early diagnostic of Spa, in particular, AS and undifferentiated spondyloarthritis.

6 Claims, 6 Drawing Sheets

Overview

| | CD74 IgG | CD74 IgA | IKBKB IgG | CD74 IgG + IgA + IKBKB IgG + Combination | CD74 IgG or IgA or IKBKB IgG positive |
|---|---|---|---|---|---|
| Sensitivity | 65% AS/ 80% USpA | 85,5% AS/ 80% USpA | 66% | 60% | 97% |
| Specifity | 96% | 92% | 96% | 100% | 72% |

Ankylosing Spondylitis (AS)
Undifferentiated Spondyloarthritis (USpA)

Figure 6

METHODS AND MEANS FOR DIAGNOSING SPONDYLARTHRITIS USING AUTOANTIBODY MARKERS

CROSS-REFERENCE TO RELATED APPLICATIONS

This application is a divisional application of U.S. Ser. No. 13/816,962 filed Apr. 23, 2013, now U.S. Pat. No. 9,915,664, which was filed as a national stage application under Rule 371 from PCT/EP2011/004098 filed Aug. 16, 2011 which claimed priority to European Application 10172861.6 filed Aug. 16, 2010.

FIELD OF THE INVENTION

The present invention relates generally to methods for diagnosing the presence or the risk of development or the therapy control of spondyloarthritis (Spa), in particular, of ankylosing spondylitis (AS) in a subject, in particular in mammals. In addition, the present invention relates to test kits for use in the diagnosis of the presence or the risk of development, or for the therapy control of Spa, like AS, in a subject. In particular, the present invention relates to a method for diagnosing the presence or the risk of development, or for the therapy control of Spa, like AS, in a subject analysing for the presence of autoantibodies against CD74 and/or IKBKB in a subject. The presence of autoantibodies against CD74 and/or IKBKB is indicative for the presence or the risk of development, or for the therapy control of Spa, like AS. In particular, detection of the presence of autoantibodies against CD74 and/or IKBKB allows early diagnosis of Spa, in particular, AS.

BACKGROUND OF THE INVENTION

Spondyloarthritis (Spa) also known as spondyloarthropathy or spondylitis identifies a group of diseases primarily affecting the spine (spondylo) and other joints. This group of diseases is also identified as seronegative spondyloarthritis. The term "seronegative" refers to the fact that usually no rheumatoid factors are present in the blood. The group of Spa can be divided into Ankylosing Spondylitis (AS), reactive arthritis and its special manifestation, Reiter syndrome, and into psoriatic arthritis (PsA), enteropathic arthritis and undifferentiated spondyloarthritis. Several of these diseases may also manifest only as peripheral arthritis without inflammation of the axial skeleton. In view of the fact that this group of diseases is a seronegative disease, early diagnosis is difficult as detailed below.

Ankylosing spondylitis (AS) also known as Morbus Bechterew is a common, inflammatory rheumatoid disease which primarily affects the axial skeleton and is associated with sacroiliitis, uveitis and enthesitis. It affects in excess of 0.1% of the population and can be associated with uveitis, apical pulmonary fibrosis and cardiac disease. AS is a member of the group of seronegative spondyloarthropathies. It is believed that genetic predisposition is given. Further, it is described in the literature that AS is an autoimmune disease. Typically, joints in the spine and the sacroilium in the pelvis are affected. Eventually, fusion of the spine may occur. The aetiology of AS is unknown, but it is thought to be immune mediated. For example, autoimmune phenomena against the proteoglycan aggrocan are described. Typically, first symptoms of the disease appears between the age of 20 to 25. Untreated patients usually suffer from morning stiffness in the lower part of the spine or sometimes the entire spine often with pain referred to one or other buttock or the back of thigh from the sacroiliac joint. Men are affected more than women. Interestingly, AS is associated with an inflammation of the eye (iridocyclitis and uveitis) in about 40% of cases.

In the course of the disease, the spine gets porous which eventually lead to rupture of the vertebrae. It is assumed that about 1.75% of the adults have a prevalence for developing AS and undifferentiated spondyloarthritis.

Diagnosis of Spa, like AS and undifferentiated spondyloarthritis, represents a challenging task for laboratory diagnosis. It is quite common for the diagnosis of Spa, like AS and undifferentiated spondyloarthritis, to be missed or remarkably delayed, particularly, in the primary care setting. For example, on average, there is a 7-10 year delay in the diagnosis of AS from the onset of symptoms. The reason for this delay is the fact that there is no direct test to diagnose Spa, like AS. Hence, Spa, like AS, undifferentiated spondyloarthritis or PsA, must be diagnosed by differential diagnosis excluding other disease with similar symptoms, like osteoarthritis, osteoporosis, herniated disk or bacterial infections. Today, clinical examination in X-ray'studies of the spine which show characteristic spinal changes and sacroilitis are the major diagnostic tools. However, X-ray studies lead to a long delay in diagnosis since the X-ray evident changes occur only after several years of onset of the disease. Although magnet resonance imaging may allow to establish early diagnosis, magnet resonance diagnosis is expensive and not every patient having pain would be diagnosed by magnetic resonance spectrometry further.

Although there is a need for diagnostic markers of Spa, like AS and undifferentiated spondyloarthritis, in particular of markers allowing early diagnosis of said diseases, no specific marker has been established yet. Several potential diagnostic markers have been described in the art. For example, variations of the HLA-B gene increase the risk of developing AS, although it is not a diagnostic test. It has been described that subjects with HLA-B27 variant are at higher risk than the general population of developing the disorder. HLA-B27 positive subjects are also indicative for other types of diseases, like Morbus Reiter as well as psoriatic arthritis but also for seropositive rheumatoid arthritis. Even 10% of healthy individuals carry the HLA-B27 antigen. Thus, false positive diagnosis may occur and the specificity of HLA-B27 for Spa, in particular, for AS and undifferentiated spondyloarthritis, is low.

Recently, anti-agalactosyl IgG antibodies in AS and psoriatic arthritis (PsA) have been described, Chou, C.-L., et al., Clin Rheumatol, 2010, DOI 10.1007/s10067-010-1413-7. However, the anti-agalactosyl IgG antibody described therein has also been described as a useful serological marker for rheumatoid arthritis. In addition, in seronegative spondyloarthropathy for which AS and PsA are representatives anti-agalactosyl IgG antibodies have been detected as well. Hence, anti-agalactosyl IgG antibody does not allow to discriminate between AS and PsA and between AS and other inflammatory rheumatic disorders.

Moreover, WO 2010/037184 describes diagnostic markers for AS. Therein, diagnostic methods and agents for diagnosing the presence or risk of development of AS in mammals are described. Said diagnostic methods and agents are based on the detection of polymorphisms within various genes. The diagnostic markers and the diagnostic test described therein are based on nucleic acid molecule detection or protein detection of the respective genes and proteins.

Very recently, screening and evaluating the mimic peptide as a useful serum biomarker of AS using the phage display technique has been described by Wang, M., et al., Rheumatol Int, DOI 10.1007/s00296-010-1403-8. Therein, the authors disclose a peptide sequence named AS1 which should represent a useful peptide reacting with sera of AS patients and, thus, may be a candidate for a specific serum biomarker. It is identified therein that the short peptide has no significant similarity with other sequences. Wright, C., et al., 2010, Mol Cell Proteomics, DOI 10.1074, mcp 11900384-MCP200, shows the detection of multiple autoantibodies in patients with AS using nucleic acid programmable protein assays.

In view of the above, there is an ongoing need for providing a diagnostic tool and method allowing diagnosis and assessing the risk of developing Spa, like AS and undifferentiated spondyloarthritis, as well as a tool and method for therapy control of Spa, like AS and undifferentiated spondyloarthritis. In addition, this tool, e.g. a kit, or method should preferably allow to differentiate between different seronegative spondyloarthropathies. In particular, the diagnostic marker may allow to differentiate between AS and PsA and between AS and other inflammatory rheumatic disorders.

BRIEF DESCRIPTION OF THE PRESENT INVENTION

The present inventors aimed to provide a diagnostic method for the presence or the risk of developing Spa, like AS, as well as for therapy control of Spa, like AS and undifferentiated spondyloarthritis, in a subject. That is, the present inventors recognised that subjects suffering from Spa, like AS and undifferentiated spondyloarthritis, have autoantibodies directed against the CD74 molecule and/or IKBKB molecule. Hence, early diagnosis of Spa, in particular AS and undifferentiated spondyloarthritis, is possible even before having X-ray evidences.

Thus, a first embodiment of the present invention relates to a method for diagnosing the presence or the risk of development, or for the therapy control of spondyloarthritis (Spa), in particular of ankylosing spondylitis (AS) and undifferentiated spondyloarthritis, in a subject comprising
a. obtaining from the subject a biological sample, and
b. analysing the sample for the presence of autoantibodies against CD74 and/or IKBKB,
whereby the presence of autoantibodies against CD74 and/or IKBKB are indicative of the presence or the risk of development, or for the therapy control of Spa, in particular, AS and undifferentiated spondyloarthritis.

Preferably, the presence of autoantibodies against both CD74 and IKBKB are determined.

Preferably, said detection of autoantibodies is conducted using immune assays, like ELISA. Typically, the biological sample to be tested is obtained from blood, in particular, serum.

Preferred, the method according to the present invention allows to discriminate between AS and PsA. Thus, the diagnostic method according to the present invention represents the first method allowing positive diagnosis of AS and undifferentiated spondyloarthritis in a subject. Diagnosis is possible at an early stage of the disease.

Another embodiment of the present invention relates to a test kit for use in a method according to the present invention, namely for diagnosing the presence or the risk of a development as well as for therapy control of Spa, like AS and undifferentiated spondyloarthritis, in a subject comprising means of determining autoantibodies against IKBKB and/or CD74 in a biological sample of a subject to be tested and instructions on how to use said test kit. Preferably, said test kit is an ELISA assay.

BRIEF DESCRIPTION OF THE DRAWINGS

FIG. 2.

FIG. 4.

DETAILED DESCRIPTION OF THE PRESENT INVENTION

Figure 1:
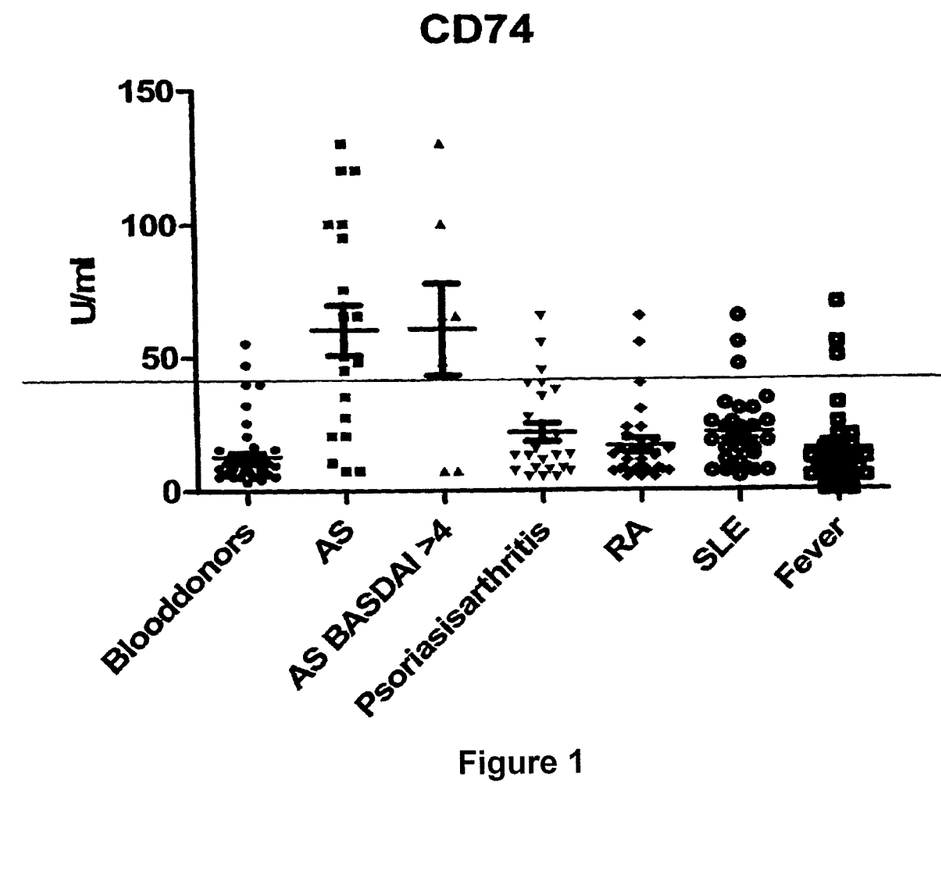
FIG. 1: The figure shows the titers of IgG-type autoantibodies against CD74 in different diseases. The titer is considered positive, if it was 40 U/ml or higher (cut-off 40 U/ml). From the left to the right the different test groups are listed: blood donors (BD), ankylosing spondylitis (AS), AS with BASDAI>4 (Bath ankylosing Spondylitis Disease Activity Index, an activity score for AS), psoriatic arthritis (PsA), rheumatoid arthritis (RA), systemic lupus erythematosus (SLE), fever.
Figure 2:
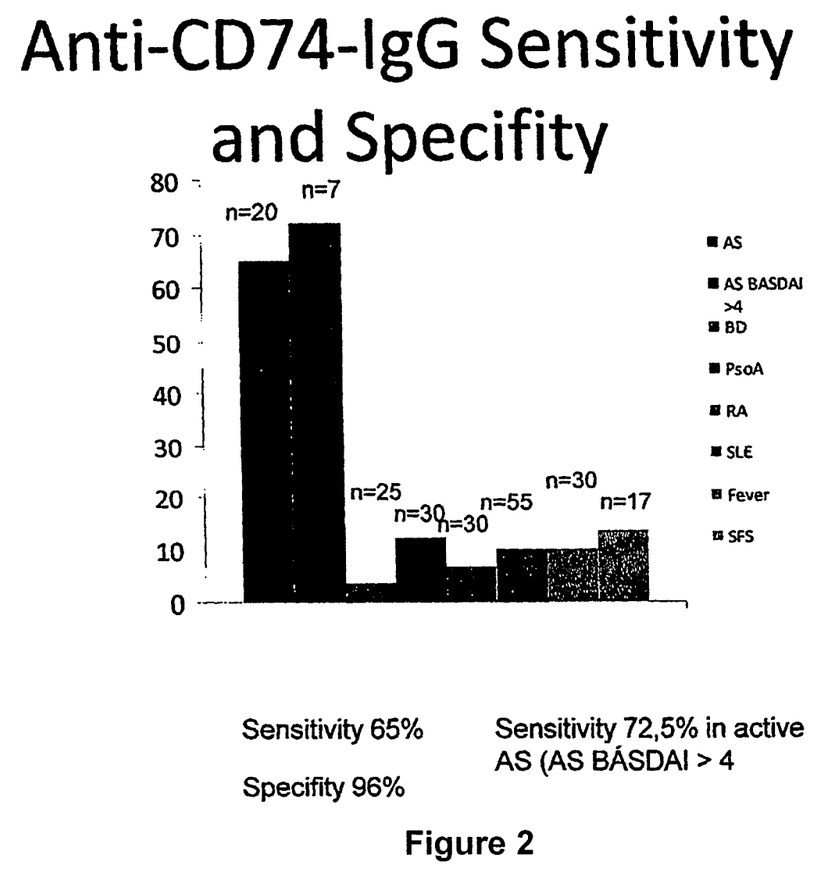
In FIG. 2 the percentage of positive results for IgG-type autoantibodies against CD74 in the following diseases is shown: ankylosing spondylitis (AS), AS with BASDAI>4, blood donors (BD), psoriatic arthritis (PsA), rheumatoid arthritis (RA), systemic lupus erythematosus (SLE), fever, chronic pain syndrome (SFS).
Figure 3:
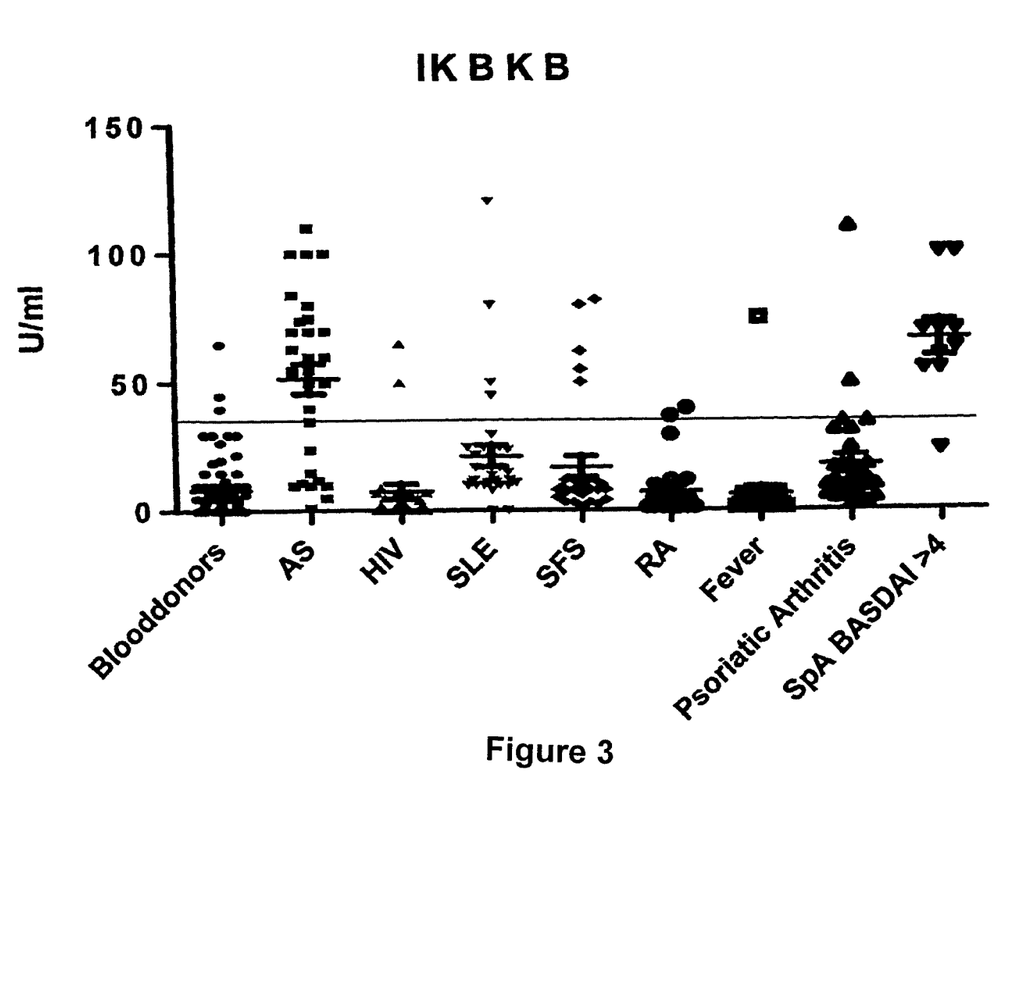
FIG. 3: The figure shows the titers of IgG-type autoantibodies against IKBKB in different diseases. The titer is considered positive, if it was 40 U/ml or higher (cut-off 40 U/ml). From the left to the right the different test groups are listed: blood donors (BD), ankylosing spondylitis (AS), HIV, systemic lupus erythematosus (SLE), chronic pain syndrome (SFS), psoriatic arthritis (PsA), rheumatoid arthritis (RA), fever, AS with BASDAI>4.
Figure 4:
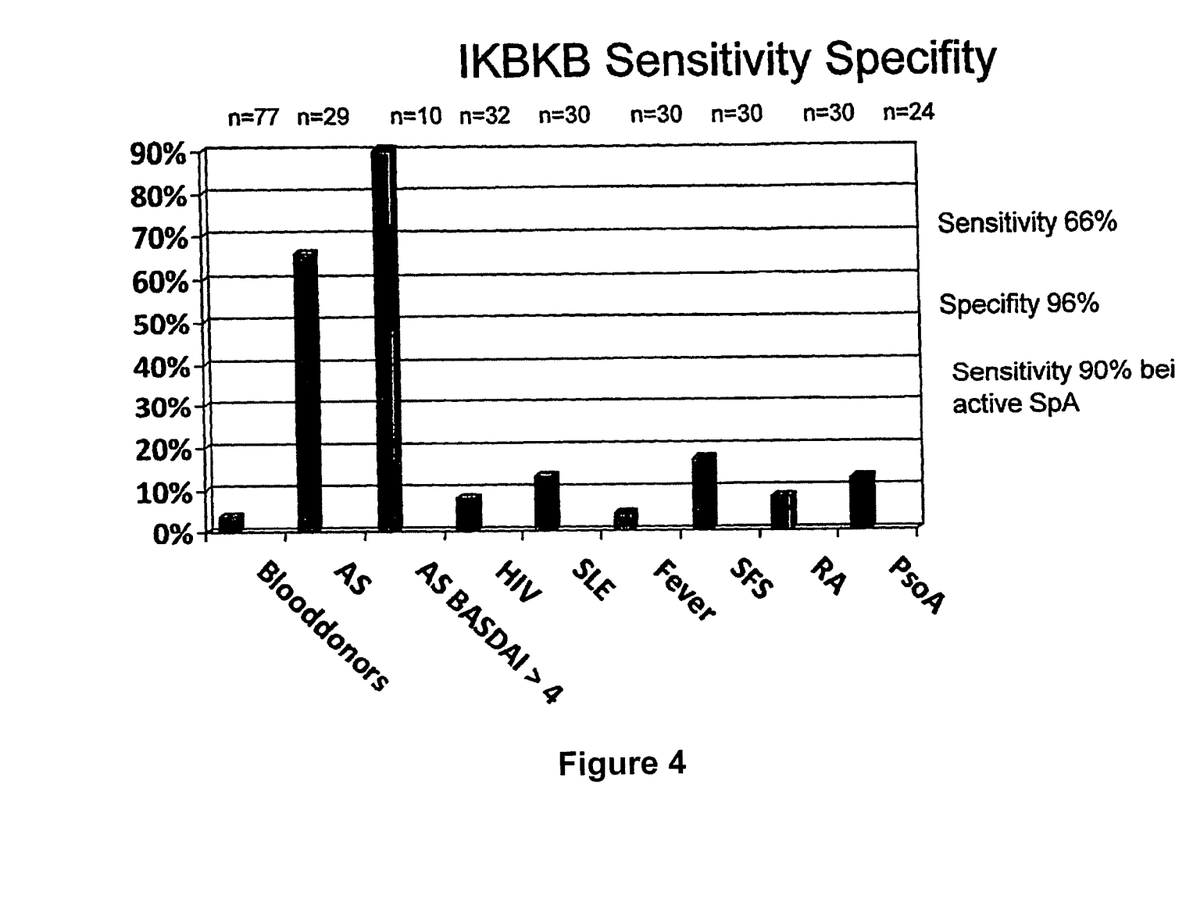
In FIG. 4 the percentage of positive results for IgG-type autoantibodies against IKBKB in the following diseases is shown: blood donors (BD), ankylosing spondylitis (AS), AS with BASDAI>4, HIV, systemic lupus erythematosus (SLE), fever, chronic pain syndrome (SFS), rheumatoid arthritis (RA), psoriatic arthritis (PsA).
Figure 5:
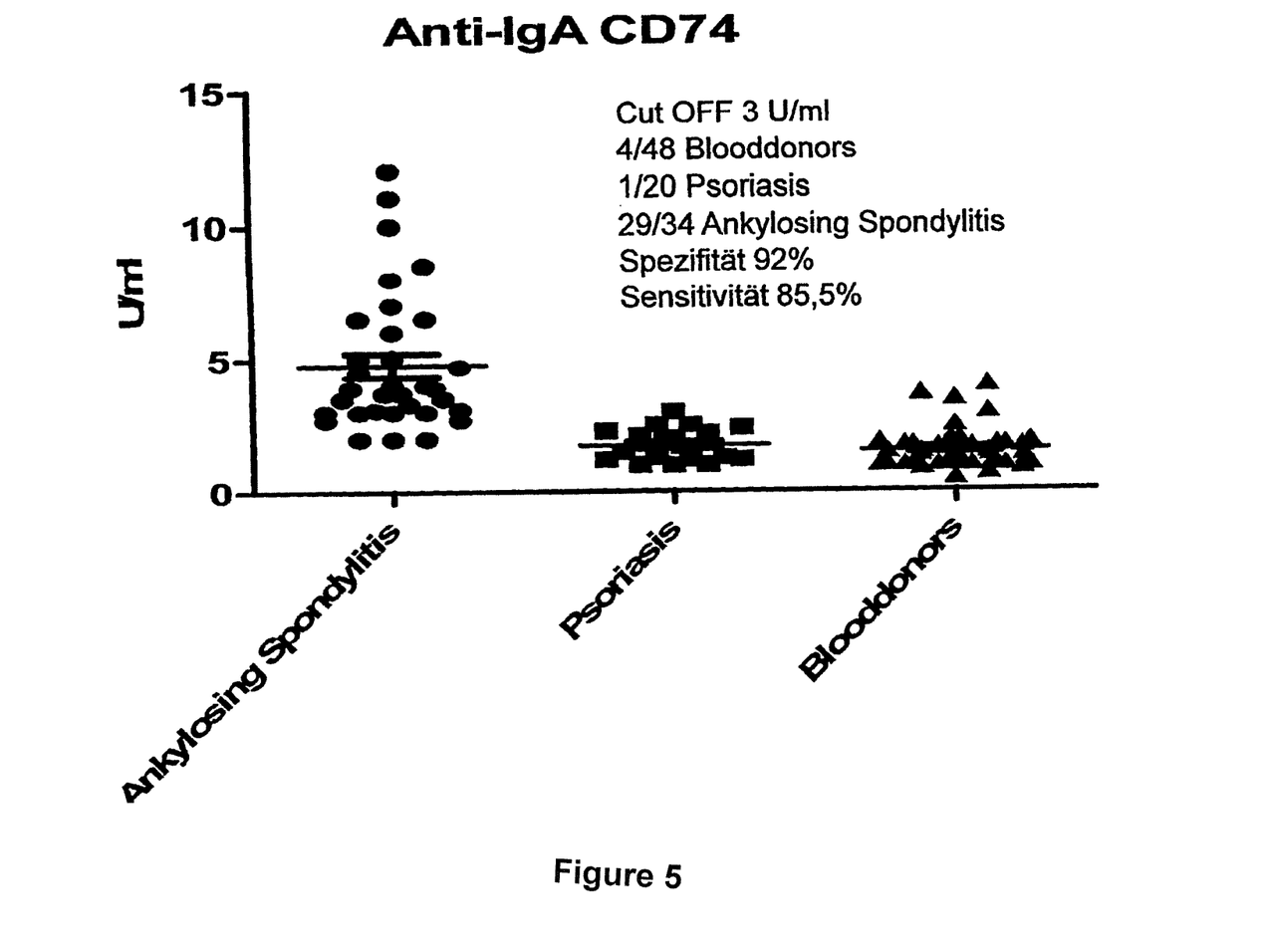
FIG. 5: The figure shows the titers of IgA-type autoantibodies against CD74 in different diseases. The titer is considered positive, if it is 5 U/ml or higher (cut-off 5 U/ml). From the left to the right the different test groups are listed: ankylosing spondylitis (AS), psoriasis, blood donors (BD).
Figure 6:
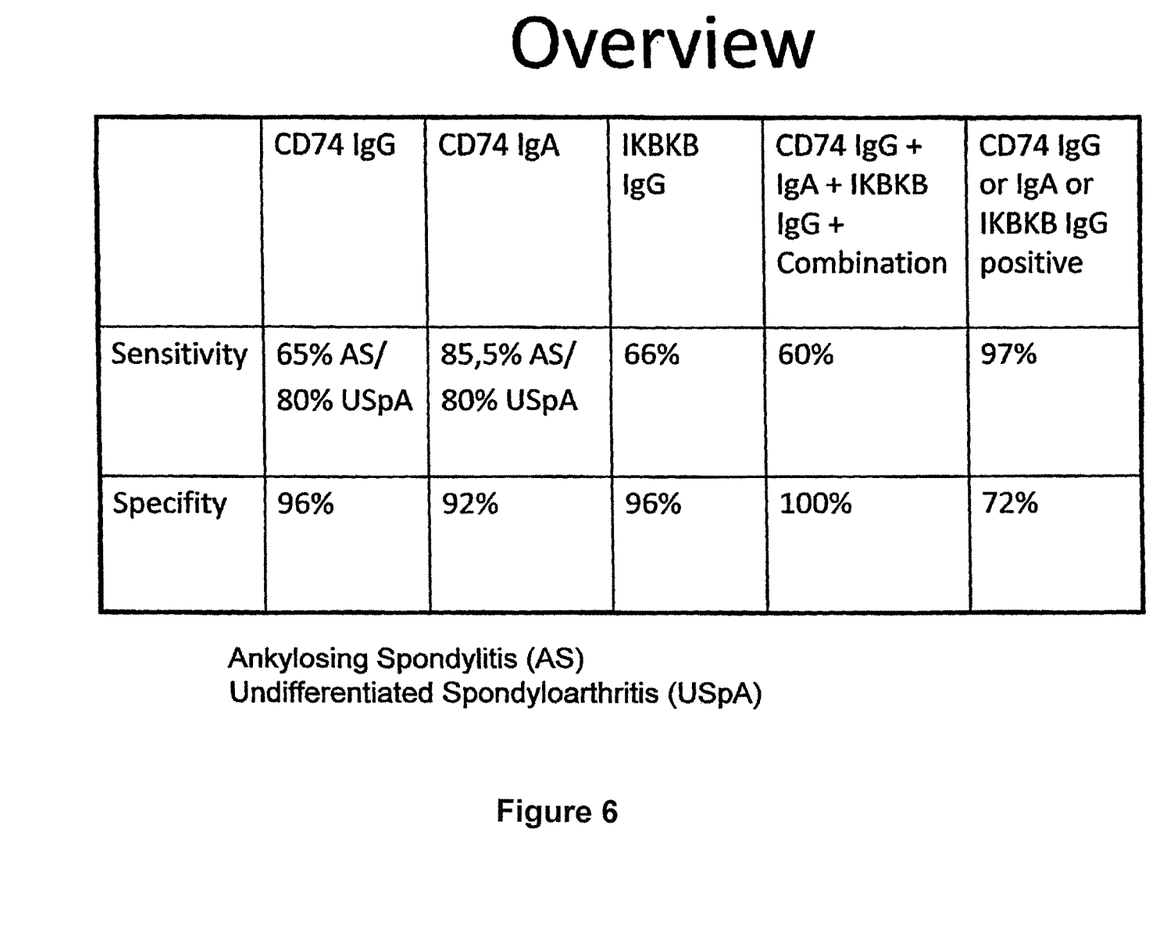
FIG. 6: The figure shows an overview of the sensitivity and specificity for AS of each autoantibody alone and in combination and for undifferentiated spondyloarthritis.

In a first aspect, the present invention relates to a method for diagnosing the presence or the risk of development, or for the therapy control of spondyloarthritis (Spa), in particular ankylosing spondylitis (AS) and undifferentiated spondyloarthritis, in a subject comprising
a. obtaining from the subject a biological sample, and
b. analysing the sample for the presence of autoantibodies against CD74 and/or IKBKB,
whereby the presence of autoantibodies against CD74 and/or IKBKB are indicative of the presence or the risk of development, or for the therapy control of Spa, like AS and undifferentiated spondyloarthritis.

That is, the present invention is based on the observation of the present inventors that subjects afflicted with Spa, like AS and undifferentiated spondyloarthritis, or having risk of developing Spa, like AS and undifferentiated spondyloarthritis, as well as for the therapy control of Spa, like AS and undifferentiated spondyloarthritis, have autoantibodies against the proteins CD74 and/or IKBKB, respectively.

With respect to the term "autoantibody" or "autoantibodies" is meant an antibody that is directed against one or more of the subjects own proteins.

IKBKB is also known as an inhibitor of nuclear factor kappa B kinase subunit beta or IKK-beta. CD74 is also known as the invariant chain of the major histocompatibility complex class II. That is, the cell surface form of the invariant chain is known as CD74.

Both proteins are expressed by a variety of cells. The present inventors demonstrate that CD74 and IKBKB alone or in combination represent entities to which autoantibodies can be found in subjects afflicted with Spa, like AS and undifferentiated spondyloarthritis. Hence, determining the presence of autoantibodies against CD74 and/or IKBKB are indicative of the presence or the risk of development, or for the therapy control of Spa, like AS and undifferentiated spondyloarthritis, in a subject. As demonstrated in the examples, the determination of autoantibodies against one of these molecules allow to identify individuals suffering from Spa, like AS and undifferentiated spondyloarthritis.

In particular, it is demonstrated herein that determining the presence of autoantibodies against CD74 and/or IKBKB allow a specific diagnosis of Spa, like AS and undifferentiated spondyloarthritis, in particular, at early stages, which was not possible before. Until today, Spa, like AS and undifferentiated spondyloarthritis, can be diagnosed by extensive and cost-intensive diagnosis or exclusion of other diseases, disorders or conditions, only. Thus, it is possible for the first time to diagnose the presence or the risk of development of Spa, like AS and undifferentiated spondyloarthritis, in a subject with a simple test system or test kit based on the method described herein. Further, it is possible to allow therapy control of subjects afflicted with Spa, like AS and undifferentiated spondyloarthritis.

For example, the present invention allows to identify the therapy regimen of an individual in need thereof. That is, identifying the presence of autoantibodies against CD74 and/or IKBKB pinpoints to a therapy comprising B-cell depletion or inducing tolerance in T-cells.

In a preferred embodiment, the presence of autoantibodies against both, CD74 and IKBKB, is determined. That is, by determining the presence of autoantibodies against both, CD74 and IKBKB, the specificity of diagnosing AS is almost 100%.

In another embodiment, methods according to the present invention allow to differentiate between seronegative spondyloarthropathies, namely to differentiate between AS and PsA. In contrast to previously suggested methods for diagnosing AS, normally including the diagnosis of PsA and does not allow differentiation between AS and PsA, the present invention enables specifically diagnosing AS while excluding PsA.

The terms "patient" and "subject" are used interchangeably and refer to patients and subjects of humans or other mammals and includes any individual it is desired to examine or treat using the methods of the invention. However, it will be understood that "patient" does not imply that symptoms are present.

The term "biological sample" as used herein refers to a sample that may be extracted, untreated, treated, isolated or concentrated from a patient. Suitably, the biological sample is selected from any part of a patient's body, including, but not limited to hair, skin, nails, tissues or body fluids, such as saliva, synovia and blood.

Throughout this specification, unless the context requires otherwise, the word "comprise" will be understood to imply the inclusion of a stated step or element or group of steps or elements but not the exclusion of any other step or element or group of steps or elements.

With the term "obtained from" is meant that a sample such as, for example, serum is isolated from or derived from a particular source of the subject. For example, the extract can be obtained from a tissue or a body fluid isolated directly from the subject.

As used herein, the terms "a", "an" and "the" mean "one ore more" when used in this application, including the claims.

Unless defined otherwise, all technical and scientific terms used herein have the same meaning as commonly understood to one of the ordinary skilled in the art to which the present disclosed subject matter belongs.

The terms "diagnosing" and "diagnosis" as used herein refers to methods by which a skilled artisan can estimate and even determine whether or not a subject is suffering from a given disease, disorder or condition. The skilled artisan makes the diagnosis on the basis of one or more diagnostic indicators, namely autoantibodies, the amount (including presence or absence) of which is indicator for the presence, severity, or absence of the condition.

Along with diagnosis, therapy control and clinical prognosis it is also an area of great concern and interest. It is important to know the severity of the disease as well as the activity of the disease in order to design the most effective therapy.

Hence, "making a diagnosis" or "diagnosing", as used herein, may further include making a prognosis which can provide for predicting a clinical outcome, selecting an appropriate treatment, or monitoring a current treatment and potentially change in the treatment based on the measure of a diagnostic autoantibody.

The term "determining" or "analysing" as used herein refers to assessing the presence, absence, quantity, level or amount of the respective autoantibodies within the subject derived sample, including qualitative or quantitative concentration levels of said substances otherwise evaluating the values or categorisation of a subject clinical parameter.

It has been determined by the inventors that autoantibody production against CD74 and/or IKBKB can be correlated with the presence of AS and undifferentiated spondyloarthritis.

In addition, in some embodiments of the presently disclosed subject matter, multiple determinations of the autoantibodies over time can be made to facilitate diagnosis and/or prognosis.

In some embodiments of the methods disclosed herein, detecting, determining or analysing the presence of the autoantibodies in the sample can include binding the autoantibodies to antigen and then detecting either the binding event or the presence of the autoantibody isolated from the biological sample. Exemplary techniques for detecting the autoantibodies include, but are not limited to, enzyme-linked immunosorbant assay (ELISA), radio immuno assay (RIA), multiplex immune assay, immunoprecipitation and immunoblotting (including for example western blotting and dot blotting).

The skilled person is well aware of useful immunodetection methods allowing analysing the sample for the presence or absence of autoantibodies against CD74 and/or IKBKB. For example, the biological sample obtained from the subject is contacted with an antigen, namely with a CD74 and/or IKBKB oligo-, polypeptide or protein representing the autoantibody immunoreactive peptide, thus, allowing binding of the autoantibody to said peptide. In this connection, the term polypeptide or protein which are used interchangeably herein, refer to a polymer of amino acids having a length of at least 50 aa. The term "oligopeptide" refers to a polymer of amino acids having a length of from 5 to 49 aa.

Contacting the chosen biological sample of the antigen under conditions effective and for a period of time sufficient to allow the formation of immune complexes, is generally a matter of adding the composition to the sample and incubating the mixture for a period of time along enough for the autoantibodies to form immune complexes with the antigens presented. Said antigen antibody mixture can be detected by known means and methods. That is, detection of immunocomplex formation of antigen autoantibody can be achieved through the application of numerous approaches. These methods are generally based upon the detection of a label or marker, such as any radioactive, fluorescent, biological or enzymatic tags or labels of standard use in the art. Of course, one may find additional advantages through the use of a secondary binding ligand such as a second antibody or a biotine/avidine (streptavidine) ligand binding arrangement as it is known in the art.

In some embodiments, the primary immune complex can be detected by a second binding ligand that has binding affinity for the antigen or the autoantibody presented in the sample, for example reactivity to the Fc region of the autoantibodies or having reactivity to a region of the antigen different to the binding region of the autoantibody. In these cases, the second binding ligand can be linked to a detectable label or marker molecule. The second binding ligand is itself often an antibody which may thus be termed a secondary antibody. Typically, the primary immune complexes are contacted with the labelled, secondary binding ligand or antibody, under conditions effective and for a period of time sufficient to allow the formation of secondary immune complexes.

The secondary immune complexes are then generally washed to remove of any unbound labelled secondary antibodies or ligands, and the remaining label in the secondary immune complex is then detected.

The second binding ligand, such as an antibody, having binding activity for either the antigen or autoantibody, may also be used to bind to the primary immune complexes. The second binding ligand contains an enzyme capable of processing a substrate detectable to a product and, hence, amplify a signal over time. After washing, the secondary immune complexes are contacted with substrate, permitting detection.

Alternatively, comparative immunodetection may be used. The skilled person is well aware of suitable methods.

It is particularly preferred that the biological sample is a body fluid, preferably blood. In particular, the biological sample is serum of the subject to be diagnosed.

As outlined before, the method according to the present invention is particularly useful for allowing differentiation between AS and PsA. Further, in another embodiment, the methods according to the present invention allows for the stratification of the therapeutic regimen of a subject afflicted with Spa, like AS and undifferentiated spondyloarthritis, or being at risk of developing Spa, like AS and undifferentiated spondyloarthritis. That is, the present invention allows to identify the status of disease, in particular, the active state of the disease in a subject afflicted with Spa, like AS and undifferentiated spondyloarthritis.

The autoantibodies to be detected may be of the IgA and/or IgG type. That is, it is possible to determine the presence of IgA and/or IgG autoantibodies in the biological sample obtained from the subject. Although it is sufficient to detect only one type of antibodies, either IgA or IgG autoantibodies, it is preferred that both IgA and IgG autoantibodies against CD74 and IKBKB are detected.

In a particular preferred embodiment, the subject is a human and the autoantibodies are human autoantibodies.

In a further embodiment, the presently disclosed subject matter provides test kits or diagnostic kits for the use in a method according to the present invention. In particular, immunological kits for use in detecting autoantibodies in biological samples allowing diagnosis of Spa, like AS and undifferentiated spondyloarthritis. That is, the present invention provides a test kit for use in a method according to the present invention for diagnosing the presence or the risk of a development as well as for the therapy control of Spa, like AS, in a subject comprising means or determining autoantibodies against IKBKB and/or CD74 in a biological sample of a subject to be tested and instructions on how to use the test kit. In a preferred embodiment, said test kit is an ELISA.

Such kits can generally comprise one or more antigens, namely, oligo- or polypeptides of CD74 and/or IKBKB that can immunoreact with the autoantibodies. Typically, the immunodetection kits will comprise in suitable container(s), one or more autoantibody immunoreactive peptide antigens derived from CD74 and/or IKBKB. Said antigens useful in the presently claimed methods and test kits may be the full CD74 and/or IKBKB protein or immunoreactive peptides derived therefrom.

In certain embodiments, the antigen can be provided bound to a solid support, such as for example a column matrix or a well of a microtiter plate, a membrane, beads, dip sticks or the like. Alternatively, the support can be provided as a separate element of the kit.

That is, the test kit according to the present invention for diagnosing Spa, like AS and undifferentiated spondyloarthritis, includes beside the antigen a detection agent for the autoantibodies which may be an antibody, antibody fragment, etc. In addition, the kit may comprise more than one detection agent. If required, the kit further comprises substrate and further means for allowing reaction with an enzyme used as label for the detecting agent which may be an antibody.

The immunodetection agents of the kit can include detectable labels that are associated with or linked to the given detecting agent, in particular, the detecting antibody. Detectable labels that are associated with or attached to a secondary binding ligand are also contemplated. Detectable labels include dyes, illuminescent or fluorescent molecules, biotine, radiolabels or enzymes. Typical examples for suitable labels include commonly known fluorescent molecules, like rhodamine, fluorescein, green fluorescent protein or luciferase, or alkaline phosphatase and horseradish peroxidase as examples for suitable enzymes.

Optionally, the kits further comprise positive and negative controls for verifying the results obtained when using the kit. The components of the kits can be packaged either in aqueous medium or lyophilised form and, in addition, the kits comprise one or more containers allowing to conduct the detection. In addition, the test kit comprises instructions for use of the kit.

Moreover, the present invention relates to the use of IKBKB and/or CD74, immune reactive sequences or analogs thereof in the diagnosis, risk assessment or therapy control of Spa, like AS and undifferentiated spondyloarthritis.

In this connection, the term "immune reactive peptides" refers to peptide fragments of IKBKB and/or CD74 enabling binding with the autoantibodies derived from the subject.

Finally, the present invention relates to the use of peptides derived from CD74 and/or IKBKB including immune reactive peptides in prophylaxis and/or treatment of Spa, in particular AS and undifferentiated spondyloarthritis. That is, the use of CD74 and/or IKBKB peptides including the immune reactive peptides of said molecules allow to induce tolerance, thus, being useful in prophylaxis and therapy of Spa, in particular AS and undifferentiated spondyloarthritis. For example, CD74 and/or IKBKB, immune reactive peptides thereof as well as analogs thereof may be used for systemic or local therapy of diseases, disorders or conditions which are associated with an immunoreaction against said compounds. The administration thereof may be effected orally, parenterally or via mucosal membranes.

Hence, the present invention provides pharmaceutical compositions containing CD74 and/or IKBKB molecules including immune reactive peptides for use in the prophylaxis and treatment of the diseases identified herein as well as in diseases, disorders or conditions associated with an immune reaction against these compounds. The pharmaceutical composition may be provided in a suitable form. The skilled person is well aware of useful forms, dosages etc.

EXAMPLES

The following examples have been included to illustrate modes of the present disclosed subject matter. In light of the present disclosure and the general level of the skilled in the art, those of skilled will appreciate that the following examples are intended to be exemplary only and that numerous changes, modifications and alterations can be employed without departing from the scope of the present disclosed subject matter.

Example 1

45 sera of patients with different inflammatory and rheumatic diseases were screened via protein microarray technology. Two new markers of spondylo-arthritis have been identified which have been evaluated further for their frequencies and associations by different ELISA.

Evaluation was effected with sera of 34 patients with AS, 10 with undifferentiated spondyloarthritis and of 55 blood donors. The patients had been well characterized with regard to the disease activity, demographic data and treatment. The sera of the patients and of the controls had been stored in a $-20°$ C. freezer until use.

For performing the ELISA tests, 96 well plates (Nunc Maxisorb) were coated with 20 µg of recombinant full-length CD74 derived from *E. coli* with GST tag, Abnova GmbH, Germany and a synthetic polypeptide of CD74, Abcam, USA, or with 20 µg of recombinant full-length IKBKB with GST tag, Abnova GmbH, Germany. The plates were incubated with wera in a 1:100 dilution in PBS for 30 to 60 minutes at room temperature. As a standard a serum of a patient with highly active AS was used. The concentration of antibodies in this serum was defined as 100 U/ml for IgG-type CD74– and IKBKB autoantibodies and 10 U/ml for IgA-type CD74 autoantibodies. After 30 to 60 minutes incubation, the plates were washed 3 times with PBS. Next, 100 µl of a secondary goat-anti-human-IgG antibody (KPL inc, USA) was added in a 1 µg/ml dilution or 100 µl of anti-human IgA antibody labelled with alkaline phosphatase, Antikorper-online, Germanyin a 1:1000 dilution. The plates were incubated for 30 min at room temperature and washed 3 times with PBS. The color reaction was performed with BluePhos, KPL, for up to 15 min according to manufacture's instructions and the ODs were read at 620 nm in an ELISA reader.

In the first tests the test for IgG-type autoantibodies against IKBKB had a sensitivity for AS of 66% (20 of 29 AS patients) and a specificity of 96% (3 of 78 blood donors), the test for IgG-type autoantibodies against CD74 has a sensitivity for AS of 65% (13 of 20 AS patients) and a specifity of 96% (2 of 55 blood donors), the test for IgA-type autoantibodies against CD74 had a sensitivity for AS of 85.5% (29 of 34 AS patients) and a specifity of 92% (4 of 48 blood donors). If these tests are combined, the sensitivity reaches 60% and the specifity of 100%. In addition, 8 of 10 individuals with undifferentiated spondyloarthiritis were positive for IgG- and IgA-type autoantibodies against CD74 (sensitivity 80%). This indicates that the autoantibodies are present before certain changes can be detected radiologically.

In addition, different autoimmune diseases and other diseases like SLE, RA, SFS, fever, psoriasis were tested. In these groups the frequency was between 5 to 15%. This indicates a high specificity for the diagnosis of Spa, in particular AS and undifferentiated spondyloarthritis.

The invention claimed is:

1. A method for diagnosis and treatment ankylosing spondylitis (AS) in a subject comprising:
   obtaining from the subject a biological sample consisting of blood or serum;
   measuring a level of inhibitor of nuclear factor kappa B kinase subunit beta (IKBKB) autoantibodies in said biological sample, wherein the IKBKB autoantibodies are IgG, comparing the measured level of the IKBKB autoantibodies in said biological sample to a control value;
   determining the subject is afflicted with AS when the measured level of the IKBKB autoantibodies is above the control value; and
   treating the subject determined to be afflicted with AS by B-cell depletion or inducing tolerance in T-cells.

2. The method of claim 1, further comprising measuring a level of CD74 autoantibodies, wherein the CD74 autoantibodies are IgG;
   comparing the measured level of CD74 autoantibodies in said biological sample to a control value for CD74;
   and wherein the step of determining the subject is afflicted with AS further includes determining the measured level of the CD74 autoantibodies is above the control value for CD74.

3. The method of claim 1, wherein said measuring step is performed using an immunoassay selected from the group consisting of ELISA, RIA, multiplex immunoassay, immunofluorescence assay, western blot, line assay, and dot blot.

4. The method of claim 1, wherein the subject is a human and the autoantibodies are human autoantibodies.

5. The method according to of claim 1, wherein both IgA and IgG autoantibodies are measured.

6. The method of claim 1, wherein said biological sample is serum.

* * * * *

UNITED STATES PATENT AND TRADEMARK OFFICE
CERTIFICATE OF CORRECTION

| | | |
|---|---|---|
| PATENT NO. | : 11,199,549 B2 | Page 1 of 1 |
| APPLICATION NO. | : 15/883126 | |
| DATED | : December 14, 2021 | |
| INVENTOR(S) | : Niklas Thomas Baerlecken | |

It is certified that error appears in the above-identified patent and that said Letters Patent is hereby corrected as shown below:

On the Title Page

Please correct the title to read:
(54) METHODS AND MEANS FOR DIAGNOSING SPONDYLARTHRITIS USING AUTOANTIBODY MARKERS In the Specification Column 1, Lines 1 - 3, please correct the title to read:
METHODS AND MEANS FOR DIAGNOSING SPONDYLARTHRITIS USING AUTOANTIBODY MARKERS Signed and Sealed this
Fifth Day of April, 2022

Drew Hirshfeld
*Performing the Functions and Duties of the*
*Under Secretary of Commerce for Intellectual Property and*
*Director of the United States Patent and Trademark Office*